United States Patent

Tani et al.

[11] Patent Number: 5,969,149
[45] Date of Patent: Oct. 19, 1999

[54] PROCESS FOR PRODUCING HEXAHYDROTHIENO[3,4-D]IMIDAZOLE-2,4-DIONES

[75] Inventors: Nobuhiro Tani, Ibaraki; Shinzo Seko, Toyonaka, both of Japan

[73] Assignee: Sumitomo Chemical Company, Limited, Osaka, Japan

[21] Appl. No.: 09/161,226

[22] Filed: Sep. 28, 1998

[30] Foreign Application Priority Data

Sep. 29, 1997 [JP] Japan ..................... 9-263487

[51] Int. Cl.$^6$ .................................. C07D 235/26
[52] U.S. Cl. ..................... 548/303.7; 548/303.1
[58] Field of Search .......................... 548/303.7

[56] References Cited

FOREIGN PATENT DOCUMENTS

| 47- 42793 | 12/1972 | Japan . |
| 48-67627 | 2/1975 | Japan . |
| 48-109021 | 5/1975 | Japan . |
| 53-27279 | 8/1978 | Japan . |
| 62-7196 B2 | 9/1979 | Japan . |
| 08217779 | 8/1996 | Japan . |
| 8-217779 | 8/1996 | Japan . |
| 10-231298 | 9/1998 | Japan . |

OTHER PUBLICATIONS

Conversion of Anhydride to Thiolactone in Biotin Synthesis– Katsura Kogure et al. (Agr. Biol. Chem. 40(8) 1657–1658, 1976).
Versuche zur Biotinsynthese, Preparation of (3aS, 6aR)–1, 3–dibenzyltetrahydro–4H–thieno [3,4–d ]imidazole–2, 4(1H)–dione. Gerecke, M. et al.Helv. Chim. Acta (1970), 53(5), 991–9, Basel/Switzerland.

Primary Examiner—Johann Richter
Assistant Examiner—Dominic Keating
Attorney, Agent, or Firm—Birch, Stewart, Kolasch & Birch, LLP

[57] ABSTRACT

There is disclosed a process for producing hexahydrothieno [3,4-d]imidazole-2,4-diones of the formula (1):

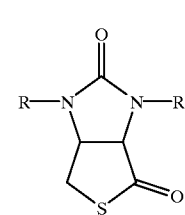

(1)

wherein R is the same or different and represents a lower alkyl group, an alkenyl group, an aryl group or an aralkyl group all of which may be substituted, which is characterized by the step of reacting hexahydrofuro[3,4-d]imidazole-2,4-diones of the formula (2):

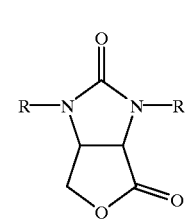

(2)

wherein R has the same meaning as described above with hydrogen sulfide in the presence of a basic compound and sulfur.

8 Claims, No Drawings

PROCESS FOR PRODUCING HEXAHYDROTHIENO[3,4-D]IMIDAZOLE-2,4-DIONES

BACKGROUND OF THE INVENTION

1. Field of the Invention

The present invention relates to a process for producing hexahydrothieno[3,4-]imidazole-2,4-diones. More particularly, the present invention concerns a process for producing hexahydrothieno[3,4-d]imidazole-2,4-diones which are useful as an intermediate for the preparation of biotin (vitamin H).

2. Description of the Related Art

Heretofore, as a method for producing hexahydrothieno[3,4-d]imidazole-2,4-diones using hexahydrofuro[3,4-d]imidazole-2,4-diones as a raw material, the following methods have been known.

1. A method in which hexahydrofuro[3,4-d]imidazole-2,4-dione is reacted with an alkali metal salt of thioacetic acid as disclosed in Helvetica Chimica Acta, 53, 991–999 (1970),
2. a method in which hexahydrofuro[3,4-d]imidazole-2,4-dione is reacted with thioarnides as disclosed in Japanese examined patent publication Shou 62-7196,
3. a method in which hexahydrofuro[3,4-d]imidazole-2,4-dione is reacted with an alkali metal salt of hydrogen sulfide as disclosed in Japanese examined patent publication Shou 51-17557, and
4. a method in which hexahydrofuro[3,4-d]imidazole-2,4-dione is reacted with an alkali metal salt of O-alkylxanthic acid as disclosed in Japanese unexamined patent publication Hei 8-217779.

However, the first method required stoichiometric amount of expensive alkali metal salt of thioacetic acid, and the second method also required expensive thioamide and was not satisfactory in yield. The third and the fourth methods are not always satisfactory in yield.

SUMMARY OF THE INVENTION

The object of the present invention is to provide an industrially advantageous process for producing hexahydrothieno[3,4-d]imidazole-2,4-diones of the following formula (1).

The present inventors have intensively studied to solve the above problem. As a result, they have found an industrially advantageous process for producing hexahydrothieno[3,4-d]imidazole-2,4-diones which are important as the intermediate of biotin, and they have accomplished the present invention.

An object of the invention is to provide:

a process for producing hexahydrothieno[3,4-d] imidazole-2,4-diones of the formula (1):

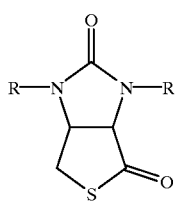

(1)

wherein R is the same or different and represents a lower alkyl group, an alkenyl group, an aryl group or an aralkyl group all of which may be substituted, which comprises: reacting hexahydrofuro[3,4-d]imidazole-2,4-diones of the formula (2):

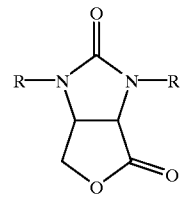

(2)

wherein R is the same meaning as defined above with hydrogen sulfide in the presence of a basic compound and sulfur.

DESCRIPTION OF THE PREFERRED EMBODIMENTS

First, a description will be made to a process for producing hexahydrothieno[3,4-d]imidazole-2,4-diones of the formula (1) as defined above, which comprises: reacting hexahydrofuro[3,4d]imidazole-2,4-diones of the formula (2) as defined above with hydrogen sulfide in the presence of a basic compound and sulfur.

In hexahydrofuro[3,4-d]imidazole-2,4-diones of the formula (2) and hexahydrothieno[3,4-d]imidazole-2,4-diones of the formula (1), R is the same or different and represents a lower alkyl group, an alkenyl group, an aryl group or an aralkyl group all of which may be substituted.

The lower alkyl group and the alkenyl group may be substituted with at least one group selected from an (C1–C3) alkoxy group, a nitro group and a halogen atom(e.g., fluorine, chlorine, bromine, iodine). Specific examples of the lower alkyl group include: a methyl group, ethyl group, n-propyl group and t-butyl group. Examples of the alkenyl group include allyl group, 2-butenyl group and 3-methyl-2-butenyl group.

The aryl group and aralkyl group may be substituted with at least one group selected from an (C1–C3)alkyl group, an (C1–C3)alkoxy group, a nitro group and a halogen atom (e.g., fluorine, chlorine, bromine, iodine). Examples of the aryl group which may be substituted include a phenyl group, a methoxyphenyl group, a nitrophenyl group and a tolyl group. Examples of the aralkyl group which may be substituted include a benzyl group, a methoxybenzyl group, a bromobenzyl group, a nitrobenzyl group, a methylbenzyl group and a phenethyl group.

Among them, benzyl group, methoxybenzyl group and allyl group are preferably employed.

Hexahydrofuro[3,4-d]imidazole-2,4-diones of the formula (2) may be optically active or racemic.

Hexahydrofuro[3,4-d]imidazole-2,4-diones, the basic compound and sulfur are usually added to a solvent and the resultant mixture is heated while blowing hydrogen sulfide into the solution. The way and the order of feeding (blowing) and the like are not limited to the above, and may be suitably changed.

Examples of the solvent used in the reaction include:
an aprotic polar amide solvent such as N,N-dimethylformamide, N,N-dimethylacetamide, 1,3-dimethyl-2-imidazolidinone, tetramethylurea, hexamethylphosphoric triamide, N-methyl-2-pyrrolidone;
an aprotic polar solvent such as dimethyl sulfoxide and sulfolane;

a glycol including polyethylene glycol and a monoether and diether thereof such as ethylene glycol, 2-methoxyethanol, dimethoxyethane, diethylene glycol, diethylene glycol monomethyl ether, diethylene glycol dimethyl ether, triethylene glycol monomethyl ether, triethylene glycol dimethyl ether;

a basic solvent such as N-methylmorpholine, diisopropylamine, triisopropylamine, tri-n-butylamine, β-picoline, γ-picoline, 2-methyl-5-ethylpyridine, quinoline, isoquinoline, N,N-dimethylaniline, N,N-diethylaniline, diazabicyclo[5,4,0]undec-7-ene; and a mixed solvent thereof.

Especially, polyethylene glycol, N,N-dimethylformamide, N,N-dimethylacetamide, 1,3-dimethyl-2-imidazolidinone, N-methyl-2-pyrrolidone, diethylene glycol monomethyl ether are preferably employed.

Although the amount of the solvent is not particularly limited, it normally is about 0.1–20 parts by weight, preferably about 1–3 parts by weight per 1 part by weight of hexahydrofuro[3,4-d]imidazole-2,4-diones from a viewpoint of volume efficiency and economics.

Examples of the basic compound used in the above reaction include an alkali metal salt of the carboxylic acid, e.g., acetic acid, propionic acid, isobutyric acid, benzoic acid, and an alkali metal hydroxide such as sodium hydroxide, potassium hydroxide; alkali metal carbonate such as potassium carbonate and sodium carbonate; an organic base such as triethylamine, triethanolamine, diisopropylamine, diisobutylamine, piperidine, pyrrolidine and N,N,N',N'-tetramethylethylenediamine. Among them, sodium acetate, potassium acetate, sodium hydroxide, potassium hydroxide and diisopropylamine are particularly preferred.

The amount of the basic compound is usually about 0.01–10 moles, preferably about 0.2–1 mol per mol of hexahydrofuro[3,4-d]imidazole-2,4-diones.

A commercially available powder sulfur is normally used as sulfur, crystalline sulfur, preferably ground crystalline sulfur, may be employed. The amount of sulfur used is usually about 0.1–20 moles, preferably about 0.1–1.2 moles per mol of hexahydrofuro[3,4-d]imidazole-2,4-diones.

The amount of hydrogen sulfide is usually about 0.5–15 moles, preferably about 1–2 moles per mol of hexahydrofuro[3,4-d]imidazole-2,4-diones.

The reaction of hexahydrofuro[3,4-d]imidazole-2,4-diones with hydrogen sulfide is usually carried out within a range of about 50–150° C., preferably within a range of about 80–110° C.

After completion of the reaction the reaction solution may be subjected to a conventional post-treatment to obtain hexahydrothieno[3,4-d]imidazole-2,4-diones of the formula (1). In this reaction, a dimeric compound of the formula (3):

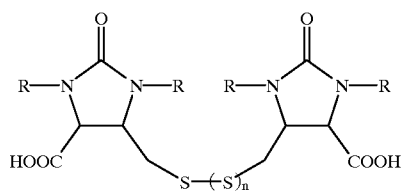

(3)

wherein R is the same as defined above and n is an integer of 1 to 5 can also be formed together with hexahydrothieno[3,4-d]imidazole-2,4-diones of the formula (1). The dimeric compound of the formula (3) can be converted to hexahydrothieno[3,4-d]imidazole-2,4-diones of the formula (1) by a reduction reaction.

The reduction reaction is carried out by using metal such as tin, zinc, iron powder or the like under an acidic condition. For example, the metal and an acid are added to the resulting reaction solution obtained by the step of reacting hexahydrofuro[3,4-d]imidazole-2,4-diones with hydrogen sulfide to improve the reaction yield and obtain the desired compound with a good quality.

Alternatively, the reduction reaction may be carried out by hydrogenation using transition metal catalyst such as palladium, platinum or nickel. The reduction reaction is preferably carried out by using zinc or iron powder under an acidic condition.

The metal which is used in the reduction may be zinc powder, iron powder and the like. The amount of the metal is normally about 0.1–5 moles, preferably about 0.5–2 moles per mol of hexahydrofuro[3,4-d]imidazole-2,4-diones.

Examples of the acid used in the above reduction include an aqueous mineral acid such as hydrochloric acid, sulfuric acid, phosphoric acid and hydrobromic acid. The amount of the acid used is normally about 0.3–15 moles, preferably about 1.5–6 moles per mol of hexahydrofuro[3,4-d] imidazole-2,4-diones.

The reduction reaction is usually carried out within a range of about 0–100° C., preferably within a range of about 25–70° C.

According to the process of the present invention, hexahydrothieno[3,4-d]imidazole-2,4-diones, which is useful as the intermediate for the preparation of biotin, can be produced industrially advantageously in a satisfactory yield by using inexpensive raw materials.

The following Examples further illustrate the present invention in detail, but are not to be construed to limit the scope of the invention.

EXAMPLE 1

After heating to 90° C. a mixture of 5.76 g of cis-1,3-dibenzylhexahydrofuro[3,4-d]imidazole-2,4-dione, 0.90 g of sodium acetate, 0.29 g of sulfur and 8.41 g of polyethylene glycol (an average molecular weight: 600), it was stirred for 7 hours at the temperature while blowing 6.66 g of hydrogen sulfide at a rate of 10 ml/minute. The amount of hydrogen sulfide consumed was 1.2 equivalents to cis-1,3-dibenzylhexahydrofuro[3,4-d]imidazole-2,4-dione, calculated from the difference between the amount of blown one and the amount of recovered one. After cooling the reaction mixture to room temperature, 33.3 g of toluene and 17.8 g of water were added to the mixture, and 1.5 g of zinc powder was further added to the mixture while stirring at room temperature. After dropping 7.4 g of 35% hydrochloric acid at room temperature, the resultant mixture was stirred at 45° C. for 3 hours and at 60° C. for another 3 hours. The mixture was separated by removing a water layer to give an oil layer, which was subjected to LC analysis. A net yield of cis-1,3-dibenzylhexahydrothieno[3,4-d]imidazole-2,4-dione was 5.59 g (yield percentage: 93%).

EXAMPLE 2

After heating to 90° C. a mixture of 5.76 g of cis-1,3-dibenzylhexahydrofuro[3,4-d]imidazole-2,4-dione, 0.90 g of sodium acetate, 0.29 g of sulfur and 8.41 g of polyethylene glycol (the average molecular weight: 600), it was stirred for 3 hours at the temperature while blowing 3.01 g of hydrogen sulfide at a rate of 10 ml/minute. Then blowing of hydrogen sulfide was stopped and the resultant mixture was stirred for 4 hours at that temperature. The amount of hydrogen sulfide consumed was 1.2 equivalents to cis-1,3-dibenzylhexahydrofuro[3,4-d]imidazole-2,4-dione, calculated from the difference between the amount of blown one and the amount of recovered one. After conducting the reduction with zinc powder and the after-treatment in the same manner as that described in Example 1, the oil layer was subjected to LC analysis. The net yield of cis-1,3-dibenzylhexahydrothieno[3,4-d]imidazole-2,4-dione was 5.71 g (yield percentage: 94%).

EXAMPLE 3

After heating to 90° C. a mixture of 5.76 g of cis-1,3-dibenzylhexahydrofuro[3,4-d]imidazole-2,4-dione, 0.43 g of sodium hydroxide, 0.29 g of sulfur and 8.41 g of polyethylene glycol (the average molecular weight: 600), it was stirred for 7 hours at that temperature while blowing 6.66 g of hydrogen sulfide at a rate of 10 ml/minute. Thereafter, the resulting mixture was subjected to reduction reaction with zinc powder and after-treatmnent as described in Example 1, obtained oil layer was subjected to LC analysis. The net yield of cis-l,3-dibenzylhexahydrothieno[3,4-d]imidazole-2,4-dione was 5.71 g (yield percentage: 94%).

EXAMPLE 4

After heating to 100° C. a mixture of 5.76 g of cis-1,3-dibenzylhexahydrofuro[3,4-d]imidazole-2,4-dione, 1.10 g of diisopropylamine, 0.29 g of sulfur and 8.41 g of polyethylene glycol (the average molecular weight: 600), it was stirred for 7 hours at the temperature while blowing 9.40 g of hydrogen sulfide at a rate of 10–30 ml/minute. Thereafter, the resulting mixture was subjected to reduction reaction with zinc powder and after-treatment as described in Example 1, obtained oil layer was subjected to LC analysis. The net yield of cis-l,3-dibenzylhexahydrothieno[3,4-d]imidazole-2,4-dione was 5.55 g (yield percentage: 92%).

EXAMPLE 5

After heating to 100° C. a mixture of 5.76 g of cis-1,3-dibenzylhexahydrofuro[3,4-d]imidazole-2,4dione, 0.75 g of potassium acetate, 0.29 g of sulfur and 8.41 g of polyethylene glycol (the average molecular weight: 600), it was stirred for 7 hours at the temperature while blowing 9.40 g of hydrogen sulfide at a rate of 10 - 30 ml/minute. Thereafter, the resulting mixture was subjected to reduction reaction with zinc powder followed by after-treatmnent as described in Example 1, obtained oil layer was subjected to LC analysis. The net yield of cis-1,3-dibenzylhexahydrothieno[3,4-d]imidazole-2,4-dione was 5.46 g (yield percentage: 90%).

EXAMPLE 6

After heating to 100° C. a mixture of 5.76 g of cis-1,3-dibenzylhexahydrofuro[3,4-d]imidazole-2,4-dione, 0.43 g of sodium hydroxide, 0.29 g of sulfur, 8.41 g of ethylene glycol and 4.20 g of 1,2-dimethoxyethane, it was stirred for 7 hours at the temperature while blowing 9.40 g of hydrogen sulfide at a rate of 10–30 ml/minute. Thereafter, the resulting mixture was subjected to reduction reaction with zinc powder and after-treatment as described in Example 1, obtained oil layer was subjected to LC analysis. The net yield of cis-1,3-dibenzylhexahydrothieno[3,4-d]imidazole-2,4-dione was 4.92 g (yield percentage: 81%).

EXAMPLE 7

After heating to 100° C. a mixture of 5.76 g of cis-1,3-dibenzylhexahydrofuro[3,4-d]imidazole-2,4-dione, 0.90 g of sodium acetate, 0.29 g of sulfur, 4.20 g of polyethylene glycol (the average molecular weight: 600) and 4.20 g of 1,2-dimethoxyethane, it was stirred for 7 hours at the temperature while blowing 9.40 g of hydrogen sulfide at a rate of 10–30 ml/minute. Thereafter, the resulting mixture was subjected to reduction reaction with zinc powder and after-treatment as described in Example 1, obtained oil layer was subjected to LC analysis. The net yield of cis-1,3-dibenzylhexahydrothieno[3,4-d]imidazole-2,4-dione was 5.49 g (yield percentage: 91%).

EXAMPLE 8

After heating to 90° C. a mixture of 32.24 g of cis-1,3-dibenzylhexahydrofuro[3,4-d]-imidazole-2,4-dione, 5.04 g of sodium acetate, 1.63 g of sulfur and 47.10 g of polyethylene glycol (the average molecular weight: 600), it was stirred for 4.5 hours at the temperature while blowing 4.09 g of hydrogen sulfide at a rate of 10 ml/minute. Then blowing of hydrogen sulfide was stopped and the resultant mixture was stirred for 4.5 hours at the temperature. After cooling the reaction mixture to room temperature, 186.34 g of toluene and 100.67 g of water were added to the mixture, and 8.14 g of zinc powder was further added to the mixture at room temperature while stirring at room temperature. After dropping 39.73 g of 35% hydrochloric acid at the same temperature, the resultant mixture was stirred at 45° C. for 6 hours. The mixture was separated by removing water layer to give an oil layer, which was subjected to LC analysis. The net yield of cis-1,3-dibenzylhexahydrothieno[3,4-d]imidazole-2,4-dione was 31.70 g (yield percentage: 94%).

EXAMPLE 9

After heating to 90° C. a mixture of 38.68 g of (+)-cis-1,3-dibenzylhexahydrofuro[3,4-d]imidazole-2,4-dione, 6.04 g of sodium acetate, 2.49 g of sulfur and 47.56 g of polyethylene glycol (the average molecular weight: 600), it was stirred for 4.5 hours at the temperature while blowing 4.50 g of hydrogen sulfide at a rate of 10 ml/minute. Then blowing of hydrogen sulfide was stopped and the resultant mixture was stirred for 5 hours at the temperature. After cooling the reaction mixture to room temperature, 173.61 g of toluene and 99.70 g of water were added to the mixture, and 8.25 g of zinc powder was further added to the mixture while stirring at room temperature. After dropping 54.90 g of 35% hydrochloric acid at the same temperature, the resultant mixture was stirred at 45° C. for 8 hours. The mixture was separated by removing water layer to give an oil layer, which was concentrated to give a product. Recrystallization from 2-propanol and water gave a crystal of (+)-cis-1,3-dibenzylhexahydrothieno[3,4-d]imidazole-2,4-dione. The yield was 36.96 g (yield percentage: 91%). Melting point was 126° C. $[\alpha]D^{20}$ was 90° C.=1.0; chloroform).

EXAMPLE 10

After heating to 90° C. a mixture of 32.24 g of cis-1,3-dibenzylhexahydrofuro[d]3,4-imidazole-2,4-dione, 5.04 g of sodium acetate, 2.08 g of sulfur and 47.56 g of N,N-dimethylformamide, it was stirred for 4.5 hours at that temperature while blowing 3.75 g of hydrogen sulfide at a rate of 10 ml/minute. Then blowing of hydrogen sulfide was stopped and the resultant mixture was stirred for 5.5 hours at that temperature. After cooling the reaction mixture to room temperature, 173.61 g of toluene and 99.70 g of water were added to the mixture, and 8.71 g of zinc powder was further added to the mixture while stirring at room temperature. After dropping 45.75 g of 35% hydrochloric acid at room temperature, the resultant mixture was stirred at 45° C. for 5 hours and at 60° C for 3 hours. The mixture was separated by removing the water layer to give an oil layer, which was subjected to LC analysis. The net yield of cis-1,3-dibenzylhexahydrothieno[3,4-d]imidazole-2,4-dione was 30.86 g (yield percentage: 92%).

EXAMPLE 11

After heating, to 90° C. a mixture of 32.24 - of cis-l1,3-dibenzylhexahydrofuro[3,4-d]imidazole-2,4-dione, 5.04 a of sodium acetate, 2.08 g of sulfur and 47.56 g of N,N-dimethylacetamide, it was stirred for 4.5 hours at the temperature while blowing 3.75 g, of hydrogen sulfide at a rate of 10ml/minute. Then blowing of hydrogen sulfide was stopped and the resultant mixture was stirred for 5.5 hours at the temperature. Thereafter, the resulting mixture was subjected to reduction reaction with zinc powder and after-treatment as described in Example 1 0, obtained oil layer was subjected to LC analysis. The net yield of cis- 1,3-dibenzylhexahydrothieno [3 ,4-d]imidazole-2,4-dione was 30.46 g (yield percentage: 90%).

EXAMPLE 12

After heating to 90° C. a mixture of 32.24 g of cis-1,3-dibenzylhexahydrofuro[3,4-d]imidazole-2,4-dione, 5.04 g of sodium acetate, 2.08 g of sulfur and 47.56 g of 3-dimethyl-2-imidazolidinone, the mixture was stirred for 4.5 hours at the temperature while blowing 3.75 g of hydrogen sulfide at a rate of 10 ml/minute. Then blowing of hydrogen sulfide was stopped and the resultant mixture was stirred for 5.5 hours at the temperature. Thereafter, the resulting mixture was subjected to reduction reaction with zinc powder and after-treatment as described in Example 10, obtained oil layer was subjected to LC analysis. The net yield of cis-1,3-dibenzylhexahydrothieno[3,4-d]imidazole-2,4-dione was 32.12 g (yield percentage: 94%).

EXAMPLE 13

After heating, to 90° C., a mixture of 32.24 g of cis-1,3-dibenzylhexahydrofuro[3,4-d]imidazole-2,4-dione, 5.04 g of sodium acetate, 2.08 g of sulfur and 47.56 g of N-methyl-2-pyrrolidone, the mixture was stirred for 4.5 hours at the temperature while blowing 3.75 g of hydrogen sulfide at a rate of 10 ml/minute. Then blowing of hydrogen sulfide was stopped and the resultant mixture was stirred for 4.5 hours at the temperature. After conducting the reduction with zinc powder followed by after-treatment as described in Example 10, obtained oil layer was subjected to LC analysis. The net yield of cis-1,3-dibenzylhexahydrothieno[3,4-d]imidazole-2,4-dione was 30.29 g (yield percentage: 90%).

EXAMPLE 14

After heating, to 90° C., a mixture of 32.24 g of cis-1,3-dibenzylhexahydrofuro[3,4-d]imidazole-2,4-dione, 5.04 g of sodium acetate, 2.08 g of sulfur and 47.56 g of diethylene glycol monomethyl ether, the mixture was stirred for 4.5 hours at the temperature while blowing 3.75 g of hydrogen sulfide at a rate of 10 ml/minute. Then blowing of hydrogen sulfide was stopped and the resultant mixture was stirred for 5.5 hours at the temperature. Thereafter, the resulting mixture was subjected to reduction reaction with zinc powder and after-treatment as described in Example 10, obtained oil layer was subjected to LC analysis. The net yield of cis-1,3-dibenzylhexahydrothieno[3,4-d]imidazole-2,4-dione was 29.78 g (yield percentage: 88%).

EXAMPLE 15

After heating to 90° C. a mixture of 32.24 g of cis-1,3-dibenzylhexahydrofuro[d]3,4-imidazole-2,4-dione, 4.05 g of potassium hydroxide(purity: 85%), 2.08 g of sulfur and 47.56 g of polyethylene glycol (the average molecular weight: 600), the mixture was stirred for 4.5 hours at the temperature while blowing 3.75 g of hydrogen sulfide at a rate of 10 ml/minute. Then blowing of hydrogen sulfide was stopped and the resultant mixture was stirred for 3.5 hours at the temperature. Thereafter, the resulting mixture was subjected to reduction reaction with zinc powder and after-treatment as described in Example 10, obtained oil layer was subjected to LC analysis. The net yield of cis-1,3-dibenzylhexahydrothieno[3,4-d]imidazole-2,4-dione was 31.51 g (yield percentage: 93%).

EXAMPLE 16

After heating to 90° C. a mixture of 32.24 g of cis-1,3-dibenzylhexahydrofuro[3,4-d]imidazole-2,4-dione, 7.75 g of potassium isobutyrate, 2.08 g of sulfur and 47.56 g of polyethylene glycol (the average molecular weight: 600), the mixture was stirred for 4.5 hours at the temperature while blowing 3.75 g of hydrogen sulfide at a rate of 10 ml/minute. Then blowing of hydrogen sulfide was stopped and the resultant mixture was stirred for 3.5 hours at the temperature. Thereafter, the resulting mixture was subjected to reduction reaction with zinc powder and after-treatment as described in Example 1, obtained oil layer was subjected to LC analysis. The net yield of cis-1,3-dibenzylhexahydrothieno[3,4-d]imidazole-2,4-dione was 30.93 g (yield percentage: 91%).

What is claimed is:

1. A process for producing hexahydrothieno[3,4-d] imidazole-2,4-diones of the formula (1):

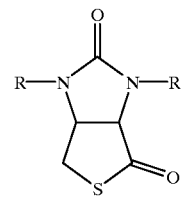

(1)

wherein R is the same or different and represents a lower alkyl group, an alkenyl group, an aryl group or an aralkyl group all of which may be substituted, which comprises:

reacting hexahydrofuro[3,4-d]imidazole-2,4-diones of the formula (2):

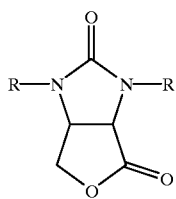

(2)

wherein R is the same meaning as defined above with hydrogen sulfide in the presence of a basic compound and sulfur.

2. A process for producing hexahydrothieno[3,4-d]imidazole-2,4-diones of the formula (1) as defined in claim 1, which comprises the steps of:

reacting hexahydrofuro[3,4-d]imidazole-2,4-diones of the formula (2) as defined in claim 1 with hydrogen sulfide in the presence of the basic compound and sulfur, and subjecting the resulting mixture to a reduction reaction.

3. A process according to claim 1 or 2, wherein the basic compound is an alkali metal salt of a carboxylic acid, a hydroxide of an alkali metal, monoalkylamine, dialkylamine or trialkylamine.

4. A process according to claim 1 or 2, wherein the amount of the basic compound is 0.2 to 1 mol per mol of hexahydrofuro[3,4-d]imidazole-2,4-diones of the formula (2).

5. A process according to claim 1 or 2, wherein the amount of sulfur is 0.2 to 1.2 moles per mol of hexahydrofuro[3,4-d]imidazole-2,4-diones of the formula (2).

6. A process according to claim 1 or 2, wherein the step of reacting hexahydrofuro[3,4-d]imidazole-2,4-diones of the formula (2) with hydrogen sulfide in the presence of the basic compound and sulfur is conducted in polyethylene glycol.

7. A process according to claim 1 or 2, wherein the step of reacting hexahydrofuro[3,4-d]imidazole-2,4-diones of the formula (2) with hydrogen sulfide in the presence of the basic compound and sulfur is conducted in an aprotic polar amide solvent or diethyleneglycol monomethyl ether.

8. A process according to claim 2, wherein the reduction reaction is conducted under acidic condition with zinc or iron powder.

* * * * *